United States Patent
Cerney

(12) 
(10) Patent No.: US 6,210,876 B1
(45) Date of Patent: *Apr. 3, 2001

(54) **NUCLEIC ACID PRIMERS AND PROBES FOR DETECTING *CHLAMYDIA PNEUMONIAE***

(75) Inventor: Michael B. Cerney, Libertyville, IL (US)

(73) Assignee: Abbott Laboratories, Abbott Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/659,473

(22) Filed: Jun. 6, 1996

(51) Int. Cl.[7] .............................. C12Q 1/68; C12P 19/34; C07H 21/04
(52) U.S. Cl. .......................... 435/6; 435/91.2; 536/23.1; 536/24.3
(58) Field of Search ..................... 435/6, 91.2; 536/23.1, 536/24.3, 24.32

(56) References Cited

U.S. PATENT DOCUMENTS

| | | |
|---|---|---|
| 5,008,186 | 4/1991 | Grayston et al. . |
| 5,281,518 | 1/1994 | Campbell et al. . |
| 5,350,673 | 9/1994 | Campbell et al. . |

FOREIGN PATENT DOCUMENTS

| | | |
|---|---|---|
| 0577144 | 1/1994 | (EP) . |
| 0587331 | 3/1994 | (EP) . |
| 9429486 | 12/1994 | (WO) . |

OTHER PUBLICATIONS

Watson et al.(IV) The nucleotide sequence of th 60 kDa cystein rich outer membrane protein of *Chlamydia psittaci* strain EAE/A22/M, Nuc. Acid. Res., vol. 18, p 5300, 1989.*

Keller and Manak, In DNA Probes, Stockton Press, chapter 1 and 7, 1993.*

Reseacrch Genetics advertisement, Aug. 11, 1994 (In NUcleic Acids Research, vol. 22.*

Tjhie, H.T.J., et al., "Detection of *Chlamydia pneumonaie* using a general Chlamydia polymerase chain reaction with species differentation after hybridisation", *Journ. Of Micro. Methods*, 18:137–150 (1993).

Gaydos, C. A., et al., "Diagnostic Utility of PCR–Enzyme Immunoassay, Culture, and Serology for Detection of *Chlamydia penumoniae* in Symptomatic and Asymptomatic Patients", *Journ. of Clin. Micro.* 32(4):903–905 (1994).

Khan, M.A., et al., "A reverse transcriptase–PCR based assay for in–vitro antibiotic susceptibility testing of *Chlamydia penumoniae*", *Journ. of Antimicrobial Chemotherapy*, 37:677–685 (1996).

Campbell, L. A., et al., "Detection of *Chlamydia pneumoniae* by Polymerase Chain Reaction", *Journ of Clinical Microbiology*, 30(2):434–439 (1992).

Gaydos, C. A., et al., "Identification of *Chlamydia pneumoniae* by DNA Amplification of the 16S rRNA Gene", *Journal of Clinical Microbiology*, 30(4):796–800 (1992).

Melgosa, M. P., et al., "Isolation and Characterization of a Gene Encoding a *Chlamydia penumoniae* 76–Kilodalton Protein Containing a Species–Specific Epitope", *Infect. and Immun.*, 62(3):880–886 (1994).

Watson, M. W., et al., "Genetic Diversity and Identification of Human Infection by Amplification of the Chlamydial 60–Kilodalton Cysteine–Rich Outer Membrane Protein Gene", *Journal of Clinical Microbiology*, 29(6):1188–1193 (1991).

George et al., "Current methods in sequence comparison analysis" in Macromolecular Sequencing And Synthesis Selected Methods And Applications, D.H. Shlesinger (ed.) pp 127–149, 1988.*

He Q. et al. Primers are Decisive for Sensitivity of PCR, Bio Techniques, vol. 17, pp 82–86, 1994.*

Watson et al. (II) Clamydia trachomatis 60 kDa cystein rich outer membrane protein: sequence homology between trachoma and LGV Biovars, FEMS Micro. Lett. vol.65, pp. 293–298, 1989.*

Watson et al. (III)The nucleotide sequnce of the 60 kDSa cystein outer membrane protein of Chlamydia pheumoniae strain IOL–207, Nuc. Acids Res. vol. 18, p. 5299, 1990.*

* cited by examiner

Primary Examiner—W. Gary Jones
Assistant Examiner—Jehanne Souaya
(74) *Attorney, Agent, or Firm*—Paul D. Yasger

(57) ABSTRACT

Nucleic acid sequences that are useful for detecting *Chlamydia pneumoniae* are herein provided. These sequences can be used in hybridization assays or amplification based assays designed to detect the presence of *Chlamydia pneumoniae* in a test sample. Additionally, the sequences can be provided as part of a kit.

8 Claims, No Drawings

NUCLEIC ACID PRIMERS AND PROBES FOR DETECTING *CHLAMYDIA PNEUMONIAE*

FIELD OF THE INVENTION

The present invention relates to *Chlamydia pneumoniae* and, in particular, it relates to oligonucleotides for detecting *Chlamydia pneumoniae* in a test sample.

BACKGROUND OF THE INVENTION

Three species within the genus Chlamydia are clinically important because of their ability to infect and cause disease in a human host. *Chlamydia trachomatis* has been reported as the most common sexually transmitted disease in industrial societies and causes genital infections in both men and women. *Chlamydia psittaci* is responsible for a variety of respiratory tract infections. The most recently characterized and clinically important member of the Chlamydia genus is *Chlamydia pneumoniae* (*C. pneumoniae*) which also is responsible for respiratory tract infections and has been associated with coronary artery disease.

Perhaps because of its fairly recent characterization, the predominant methods for detecting *C. pneumoniae* in a test sample include isolation of the organism in culture, and serology testing. Isolation may include growing the organism in tissue culture cells to produce inclusion bodies which are then detected by fluorescently staining the inclusion bodies using a labeled species-specific-antibody. Serological testing requires two samples from an individual suspected of being infected with *C. pneumoniae*. Two samples are necessary because a significant number of individuals have antibodies to *C. pneumoniae* and a rise in antibody titer to *C. pneumoniae* or a change in antibody class (e.g. IgM to IgG) is measured as an indication of a recent *C. pneumoniae* infection. Because a rise in antibody titer or a change in antibody class is measured, acute and convalescent serum samples are taken. Unfortunately, these samples are often times taken weeks or even months apart. Hence, detecting a *C. pneumoniae* infection can be a time consuming process. Accordingly, there is a need for methods and reagents capable of detecting *C. pneumoniae* in a specific and timely manner.

SUMMARY OF THE INVENTION

The present invention provides nucleic acid sequences that can be used to specifically detect *C. pneumoniae* by using these sequences as oligonucleotide probes and/or primers. Such primers or probes are designated SEQ ID NO 2, SEQ ID NO 3, SEQ ID NO 4, SEQ ID NO 5, SEQ ID NO 6, SEQ ID NO7, SEQ ID NO 9, SEQ ID NO 10, SEQ ID NO 11, SEQ ID NO 12, SEQ ID NO 13 and SEQ ID NO 14. Those skilled in the art will recognize that homologs of these sequences and combinations of these sequences can also be employed to detect *C. pneumoniae* in a test sample. Preferably, the sequences are employed in amplification reactions and can be provided in kits along with other reagents for performing an amplification reaction.

Methods provided by the present invention include hybridization assays as well as amplification based assays. Thus, according to one method, a method of detecting the presence of *C. pneumoniae* in a test sample may comprise the steps of (a) contacting the test sample with one or more of the sequences listed above, or their homologs; and (b) detecting hybridization between the above sequences and a *C. pneumoniae* target sequence as an indication of the presence of *C. pneumoniae* in the test sample.

According to another embodiment, a method for detecting the presence of *C. pneumoniae* in a test sample may comprise the steps of (a) forming a reaction mixture comprising nucleic acid amplification reagents, a test sample containing a *C. pneumoniae* target sequence, and at least one primer and one probe oligonucleotide selected from the group consisting of SEQ ID NOs. 2 and 5; SEQ ID NOs. 3 and 4; SEQ ID NOs. 2, 3 and 4; SEQ ID NOs. 2, 3 and 5; SEQ ID NOs. 2, 3, 4 and 5; SEQ ID NOs. 9 and 11; SEQ ID NOs. 10 and 12; SEQ ID NOs. 9, 10 and 11; SEQ ID NOs. 9, 10 and 12; or SEQ ID NOs. 9, 10, 11 and 12; (b) subjecting the mixture to hybridization conditions to generate at least one nucleic acid sequence complementary to the target sequence; (c) hybridizing the probe to the nucleic acid sequence complementary to the target sequence, so as to form a complex comprising the probe and the complementary nucleic acid sequence; and (d) detecting the so-formed complex as an indication of the presence of *C. pneumoniae* in the sample.

According to another embodiment, the invention provides kits which comprise a set of oligonucleotide primers and probes, selected from the SEQ ID NOs. listed above, and amplification reagents.

DETAILED DESCRIPTION OF THE INVENTION

As previously mentioned, the present invention provides nucleic acid sequences, methods for using these sequences and kits containing these sequences, all of which can be employed to specifically detect *C. pneumoniae*. The sequences provided are designated herein as SEQ ID NOs. 2, 3, 4, 5, 6, 7, 9, 10, 11, 12, 13, 14 and homologs thereof. These sequences are derived from a *C. pneumoniae* gene encoding a cysteine rich outer-membrane-protein (OMP) disclosed in Watson, M. W., et. al, *Journal of Clinical Microbiology*, 29(6) p. 1188–1193 (1991) and a *C. pneumoniae* gene encoding a 76 Kilodalton protein (76 kD protein) disclosed in Perez-Melgosa, M., et. al., *Infection and Immunity*, 62(3) p. 880–886 (1994).

With respect to the sequences herein provided, the term "homologs" means those sequences sharing about 80% homology with SEQ ID NOs. 2–7 and 9–14, and more preferably those sequences that share about 90% homology with SEQ ID NOs. 2–7 and 9–14. Thus, sequences that contain about 80% homology with the sequences provided herein and specifically hybridize with *C. pneumoniae* are intended to be within the scope of the present invention. For example, extensions of the present sequences, sequences that are shorter than the present sequences but contain a subset of the present sequences, and those sequences that deviate from the present sequences by minor base substitutions are contemplated as within the scope of the present invention.

Those skilled in the art will recognize various modifications that can be made to the sequences designated SEQ ID NOs. 2–7 and 9–14 without departing from their ability to specifically detect *C. pneumoniae* and share about 80% homology with these sequences. For example, 3' or 5' extensions of the present sequences with bases that are complementary to succeeding or preceding bases in either the OMP gene or 76 kD protein gene are considered to be homologs of the present sequences when they share about 80% homology with the present sequences and specifically detect *C. pneumoniae*. Additionally, 3' or 5' extensions of present sequences with bases that are not complementary to succeeding or preceding bases in the OMP gene or 76 kD protein gene that share about 80% homology with the present sequences and specifically detect *C. pneumoniae* are contemplated as within the scope of the present invention. Further, base substitutions can be made to SEQ ID NOs. 2–7 and 9–14, but these modified sequences will nevertheless maintain the ability to specifically hybridize with *C. pneumoniae* and share about 80% homology with SEQ ID NOs. 2–7 and 9–14. They are therefore contemplated as within the scope of the present invention. Moreover, sequences that contain about 80% of the sequences designated SEQ ID NOs. 2–7 and 9–14 but have bases deleted from the 3' or 5' end, are considered to be within the scope of the term homolog.

The sequences disclosed herein, as well as their homologs, may comprise deoxyribonucleic acid (DNA), ribonucleic acid (RNA) or nucleic acid analogs such as uncharged nucleic acid analogs including but not limited to peptide nucleic acids (PNAs) which are disclosed in International Patent Application WO 92/20702 or morpholino analogs which are described in U.S. Pat. No. 5,185,444, 5,034,506, and 5,142,047 all of which are herein incorporated by reference. Such sequences can routinely be synthesized using a variety of techniques currently available. For example, a sequence of DNA can be synthesized using conventional nucleotide phosphoramidite chemistry and the instruments available from Applied Biosystems, Inc, (Foster City, Calif. ); DuPont, (Wilmington, Del.); or Milligen, (Bedford, Mass.). Similarly, and when desirable, the sequences can be labeled using methodologies well known in the art such as described in U.S. patent applications Nos. 5,464,746; 5,424,414; and 4,948,882 all of which are herein incorporated by reference.

The term "label " as used herein means a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, light, and the like to enable detection of the label. When indirectly detectable labels are used, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

Generally, the sequences provided herein can be employed to detect the presence of *C. pneumoniae* in a test sample by contacting a test sample with at least one of the sequences provided herein under hybridizing conditions and detecting hybridization between the *C. pneumoniae* target sequence and at least one of the sequences designated herein as SEQ ID NOs. 2–7 and 9–14. Several well known methods for detecting hybridization can be employed according to the present invention and may include, for example, the use of gels and stains or detecting a label associated with one or more of the sequences provided herein after performing, for example, a dot blot or amplification reaction.

The term "test sample" as used herein, means anything suspected of containing the target sequence. The test sample can be derived from any biological source, such as for example, blood, bronchial alveolar lavage, saliva, throat swabs, ocular lens fluid, cerebral spinal fluid, sweat, sputa, urine, milk, ascites fluid, mucous, synovial fluid, peritoneal fluid, amniotic fluid, tissues such as heart tissue and the like, or fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma from blood, disrupting cells, preparing liquids from solid materials, diluting viscous fluids, filtering liquids, distilling liquids, concentrating liquids, inactivating interfering components, adding reagents, and the like.

A "target sequence" as used herein means a nucleic acid sequence that is detected, amplified, both amplified and detected or otherwise is complementary to one of the sequences herein provided. Thus, a target sequence will be approximately 80% complementary with the sequences provided herein. Additionally, while the term target sequence is sometimes referred to as single stranded, those skilled in the art will recognize that the target sequence may actually be double stranded.

"Hybridization" or "hybridizing" conditions are defined generally as conditions which promote annealing between complementary nucleic acid sequences or annealing and extension of one or more nucleic acid sequences. It is well known in the art that such annealing is dependent in a rather predictable manner on several parameters, including temperature, ionic strength, sequence length and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures which are slightly below the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Once sequences are selected for a given diagnostic application, the G:C content and length will be known and can be accounted for in determining precisely what hybridization conditions will encompass. Since ionic strength is typically optimized for enzymatic activity, the only parameter left to vary is the temperature. For improved specificity, the hybridization temperature is selected slightly below the Tm of the primers or probe; typically 2–10° C. below the Tm. Thus, obtaining suitable hybridization conditions for a particular primer, probe or primer and probe set is well within ordinary skill of one practicing this art.

The sequences provided herein also can be used as amplification primers or probes according to amplification procedures well known in the art. Such reactions include, but are not intended to be limited to, the polymerase chain reaction (PCR) described in U.S. Pat. Nos. 4,683,195 and 4,683,202, the ligase chain reaction (LCR) described in EP-A-320 308, and gap LCR (GLCR) described in U.S. Pat. No. 5,427,930 all of which are herein incorporated by reference.

According to a preferred embodiment, the sequences are employed in the "oligonucleotide hybridization PCR" (variably referred to herein as "OH PCR") amplification reaction as described in U.S. patent application serial No. 08/514,704, filed Aug. 14, 1995, that is herein incorporated by reference. Briefly, the reagents employed in the preferred method comprise at least one amplification primer and at least one internal hybridization probe, as well as other reagents for performing an amplification reaction.

The primer sequence is employed to prime extension of a copy of a target sequence and is labeled with either a capture label or a detection label. The probe sequence is used to hybridize with the sequence generated by the primer sequence, and typically hybridizes with a sequence that does not include the primer sequence. Similarly to the primer sequence, the probe sequence is also labeled with either a capture label or a detection label with the caveat that when the primer is labeled with a capture label the probe is labeled with a detection label and vice versa. Detection labels have the same definition as "labels" previously defined and "capture labels" are typically used to separate extension products, and probes associated with any such products, from other amplification reactants. Specific binding members (as previously defined) are well suited for this purpose. Also, probes used according to this method are preferably blocked at their 3' ends so that they are not extended under hybridization conditions. Methods for preventing extension of a probe are well known and are a matter of choice for one skilled in the art. Typically, adding a phosphate group to the 3' end of the probe will suffice for purposes of blocking extension of the probe.

"Other reagents for performing an amplification reactions" or "nucleic acid amplification reagents" include reagents which are well known and may include, but are not limited to, an enzyme having polymerase activity, enzyme cofactors such as magnesium; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

The preferred method generally comprises the steps of (a) forming a reaction mixture comprising nucleic acid amplification reagents, at least one hybridization probe, at least one amplification primer and a test sample suspected of containing a target sequence; (b) subjecting the mixture to hybridization conditions to generate at least one copy of a nucleic acid sequence complementary to the target sequence; (c) hybridizing the probe to the nucleic acid sequence complementary to the target sequence, so as to form a hybrid comprising the probe and the nucleic acid sequence complementary to the target sequence; and (d) detecting the hybrid as an indication of the presence of C. pneumoniae in the sample. It will be understood that step (b) of the above method can be repeated several times prior to step (c) by thermal cycling the reaction mixture as is well known in the art.

According to the above method, it is preferable to select primers and probes such that the probe sequence has a lower melt temperature than the primer sequences so that upon placing the reaction mixture under hybridization conditions copies of the target sequence or its complement are produced at temperature above the Tm of the probe. After such copies are synthesized, they are denatured and the mixture is cooled to enable the formation of hybrids between the probes and single stranded copies of the target or its complement. The rate of temperature reduction from the denaturation temperature down to a temperature at which the probes will bind to single stranded copies is preferably quite rapid (for example 8 to 15 minutes) and particularly through the temperature range in which an enzyme having polymerase activity is active for primer extension. Such a rapid cooling favors copy sequence/probe hybridization rather that primer/copy sequence hybridization.

Upon formation of the copy sequence/probe hybrids, the differential labels (i.e. capture and detection labels) on the copy sequence and probe sequence can be used to separate and detect such hybrids. Preferably, detection is performed according to the protocols used by the commercially available Abbott LCx® instrumentation (Abbott Laboratories; Abbott Park, Ill.).

Thus, keeping the preferred method in mind, the sequences of the present invention are preferably provided in groups of at least two different sequences (i.e. at least one primer sequence and at least one probe sequence complementary to the extension product of the primer). Hence, SEQ ID NOs. 2 and 5; SEQ ID NOs. 3 and 4; SEQ ID NOs. 2, 3 and 4; SEQ ID NOs. 2, 3 and 5; SEQ ID NOs. 2, 3, 4 and 5; SEQ ID NOs. 9 and 11; SEQ ID NOs. 10 and 12; SEQ ID NOs. 9, 10 and 11; SEQ ID NOs. 9, 10 and 12; or SEQ ID NOs. 9, 10, 11 and 12; or homologs of these sequences are preferably provided together.

The sequences of the present invention can be provided as part of a kit useful for detecting C. pneumoniae. The kits comprise one or more suitable containers containing one or more sequences according to the present invention, an enzyme having polymerase activity, and deoxynucleotide triphosphates. Typically, at least one sequence bears a label, but detection is possible without this.

The following examples are provided to further illustrate the present invention and not intended to limit the invention.

EXAMPLES

The following examples demonstrate use of the DNA oligomer primers and probes provided herein for detecting C. pneumoniae. The primers and probes used in the examples are identified as SEQUENCE ID NO 2, SEQUENCE ID NO 3, SEQUENCE ID NO 4, SEQUENCE ID NO 9, SEQUENCE ID NO 10, and SEQUENCE ID NO 11. SEQUENCE ID NOs 2, 3 and 4 are specific for the gene encoding the 60kD cysteine rich outer major protein (OMP) of C. pneumoniae, a portion of which is designated herein as SEQ ID NO 1. SEQUENCE ID NO 9, 10 and 11 are specific for the gene encoding the 76kD protein of C. pneumoniae, a portion of which is designated herein as SEQ ID NO 8. In the following examples, SEQUENCE ID NOs 2 and 3 are used as C. pneumoniae amplification primers specific for the OMP region. SEQ ID NO 4 is used as an internal hybridization probe for the OMP amplification product. SEQ ID NOs 9 and 10 are used as amplification primers specific for the 76kD region of C. pneumoniae and SEQ ID NO 11 is used as an internal hybridization probe for the 76kD amplification product.

In the following examples, "positive-control C. pneumonia sequences" (variably referred to as the "C. pneumoniae standard") were derived from C. pneumoniae cell lines TW-183, AR-39 and CWL-029 (obtained from the American Type Culture Collection -ATCC-, Rockville, Md.). The sequences were obtained by mixing equal numbers of cells from all three cell lines and collecting DNA with the QIAgen nucleic acid purification method (QIAgen, Inc., Chatsworth, Calif.).

Example 1

Preparation of C. pneumoniae Primers and Probes

A. OMP Primers and Probe

Target-specific primers and probes were designed to detect the C. pneumoniae OMP target sequence by oligonucleotide hybridization PCR. The primers were SEQUENCE ID NO 2 and SEQUENCE ID NO 3. Primer sequences were synthesized using standard oligonucleotide synthesis methodology and haptenated with adamantane at their 5' ends using standard cyanoethyl phosphoramidite coupling chemistry as described in U.S. Pat. No. 5,424,414 incorporated herein by reference.

The detection probe was designed to hybridize with the amplified C. pneumoniae OMP target sequence by oligonucleotide hybridization. This probe is SEQUENCE ID NO 4. The probe sequence was synthesized using standard oligonucleotide synthesis methodology and haptenated with 2 carbazoles at the 5' end using standard cyanoethyl phosphoramidite coupling chemistry as described in U.S. Pat. No. 5,464,746 (herein incorporated by reference), and blocked with phosphate at the 3' end. Reactivity was assessed against the C. pneumoniae standard.

B. 76kD Primers and Probe

Target-specific primers and probes were designed to detect the C. pneumoniae 76kD target sequence by oligonucleotide hybridization PCR. The primers were SEQUENCE ID NO 9 and SEQUENCE ID NO 10. Primer sequences were synthesized using standard oligonucleotide synthesis methodology and haptenated with adamantane at their 5' ends using standard cyanoethyl phosphoramidite coupling chemistry U.S. Pat. No. 5,424,414.

The detection probe was designed to hybridize with the amplified C. pneumoniae 76kD target sequence by oligonucleotide hybridization. This probe is SEQUENCE ID NO 11. The probe sequence was synthesized using standard oligonucleotide synthesis methodology and haptenated with 2 carbazoles at the 5' end using standard cyanoethyl phosphoramidite coupling chemistry (as above) and blocked with phosphate at the 3' end. Reactivity was assessed against the C. pneumoniae standard.

Example 2

Amplification and Detection of C.pneumoniae

A. C. pneumoniae OMP Detection.

The C. pneumoniae standard sample was PCR amplified and detected using the OMP primers (SEQ ID NO 2 and 3) and OMP detection probe (SEQ ID NO 4) described in Example 1.A. The primers were used at a concentrations of 0.2 µM each. Taq polymerase was used at a concentration of 2.5 units. PCR extension was performed using 10×PCR buffer (Perkin Elmer, Foster City, Calif.) which consists of 100 mM Tris-HCl, pH 8.3, 500 mM KCl, at a final concentration of 1×. The final concentration of $MgCl_2$ was 2 mM and the final concentration of the nucleotides was 0.2 mM each, in a total reaction volume of 0.2 ml.

The reaction mixture was amplified in a Perkin-Elmer 480 Thermal Cycler under the following cycling conditions: 97° C. for 30 seconds/59° C. for 30 seconds/72° C. for 30 seconds for 40 cycles.

Following amplification, a 100 µl aliquot from the above reaction mixture was added to a separate tube containing 10 µl of the detection probe at a concentration of 40 nM (therefore final detection probe concentration was 3.6 nM). After an initial denaturation step at 97° C. for 5 minutes, probe oligo hybridization was accomplished by lowering the temperature to 15° C. for 10 minutes.

Following probe hybridization, reaction products were detected on the Abbott LCx® system (available from Abbott Laboratories, Abbott Park, Ill.). A suspension of anti-carbazole antibody coated microparticles and an anti-adamantane antibody/alkaline phosphatase conjugate (all of which are commercially available from Abbott Laboratories, Abbott Park, Ill.) were used in conjunction with the LCx® to capture and detect the reaction products. The LCx® showed a positive reaction rate of 1144.1 c/s/s using the OMP primer/probe set to detect C. pneumoniae.

B. C. pneumoniae 76kD detection.

The C. pneumoniae standard sample was PCR amplified and detected using the 76kD primers (SEQ ID NO 9 and 10) and 76kD detection probe (SEQ ID NO 11) described in Example 1.B. Concentrations of reagents used in this example were the same as those used in Example 2.A. above.

The reaction mixture was amplified, followed by probe oligo hybridization as in 2.A. above.

Following probe hybridization, reaction products were detected on the Abbott LCx® system, as above in Example 2.A. The LCx® showed a positive reaction rate of 994.0 c/s/s using the 76kD primer/probe set to detect C. pneumoniae.

Example 3

Specificity of C. pneumoniae Detection

DNA from two other members of the genus Chlamydia, C. psittaci and C. trachomatis, was purchased from ABI (Advanced Biotechnologies, Inc., Columbia, Md.), diluted to levels representing $7.1 \times 10^4$ and $1.26 \times 10^5$ elementary bodies, respectively, and assayed side by side with the C. pneumoniae standard from Example 2, as described below.

A. Specific Detection of C. pneumoniae Using the OMP Primers and Probe

The OMP primers (SEQ ID NO 2 and SEQ ID NO 3) and OMP detection probe (SEQ ID NO 4) described in Example 1 were used to amplify and detect 3 samples from the genus Chlamydia (TABLE 1) by the method described in 2.A. above. The data from this experiment is presented in TABLE 1 and shows specific amplification and detection of C. pneumoniae only, with the 2 other Chlamydia genus samples being non-reactive.

TABLE 1

| Sample | LCx ® rate (c/s/s) |
| --- | --- |
| C. psittaci | 26.2 |
| C. trachomatis | 23.9 |
| C. pneumoniae (Positive Control) | 1144.1 |

B. Specific Detection of C. pneumoniae Using the 76kD Primers and Probe

The 76kD primers (SEQ ID NO 9 and SEQ ID NO 10) and 76kD detection probe (SEQ ID NO 11) described in Example 1 were used to amplify and detect 3 samples from the genus Chlamydia (TABLE 2) by the method described in 2.B. above. The data from this experiment is presented in TABLE 2 and shows specific amplification and detection of C. pneumoniae only, with the 2 other Chlamydia genus samples being non-reactive.

TABLE 2

| Sample | LCx ® rate (c/s/s) |
|---|---|
| C. psittaci | 47.1 |
| C. trachomatis | 34.5 |
| C. pneumoniae (Positive Control) | 994.0 |

Example 4

Sensitivity of C. pneumoniae Detection

A panel of C. pneumoniae cells which had been quantified using immunofluorescence to determine the number of Inclusion Forming Units (IFU) in each sample, were lysed and tested by the current methodology. Salmon sperm DNA was used as a negative control and the C. pneumoniae standard DNA as a positive control.

A. Sensitivity of the C. pneumoniae OMP Primers and Probe

The OMP primers (SEQ ID NO 2 and SEQ ID NO 3) and OMP detection probe (SEQ ID NO 4), described in Example 1, were used to amplify and detect a quantified panel of C. pneumoniae cells (TABLE 3) by a unit dose modification of the method used in Examples 2 and 3, namely: the primers, at a concenetration of 0.3 µM each, detection probe, at a concentration of 8 nM, as well as the other reagents were added to a single amplification vessel. Taq polymerase was used at a concentration of 2.5 units. PCR extension was performed in 10×PCR buffer (Perkin Elmer, Foster City, Calif.) which consists of 100 mM Tris-HCl, pH 8.3, 500 mM KCl, at a final concentration of 1×. The final concentration of $MgCl_2$ was 2 mM and the final concentration of the nucleotides was 0.2 mM each, in a total reaction volume of 0.2 ml.

The reaction mixture was amplified in a Perkin-Elmer 480 Thermal Cycler under the following cycling conditions: 97° C. for 30 seconds/59° C. for 30 seconds/72° C. for 30 seconds for 40 cycles. After maintaining the reaction mixture at 97° C. for 5 minutes, probe oligo hybridization was accomplished by lowering the temperature to 15° C. for 10 minutes.

Following probe hybridization, reaction products were detected on the Abbott LCx® system. The data from this experiment is presented in TABLE 3 and shows detection of C. pneumoniae at concentrations as low as 0.06 IFU/reaction.

TABLE 3

| Sample # | C. pneumaniae (IFU/reaction) | LCx ® rate (c/s/s) |
|---|---|---|
| 1 | 50000.00 | 2305 |
| 2 | 12500.00 | 2320 |
| 3 | 15625.00 | 2341 |
| 4 | 3906.25 | 2215 |
| 5 | 976.56 | 2361 |
| 6 | 244.14 | 2262 |
| 7 | 61.04 | 2329 |
| 8 | 15.26 | 2262 |
| 9 | 3.81 | 2302 |
| 10 | 0.95 | 2241 |
| 11 | 0.06 | 1804 |
| 12 | 0.05 | 29 |

Additional testing was performed in triplicate at concentrations below 1 IFU/reaction. The results, shown in TABLE 4, indicate consistent detection of C. pneumoniae at concentrations of 0.38 IFU/reaction.

TABLE 4

| Sample # | C. pneumoniae (IFU/reaction) | LCx ® rate (c/s/s) |
|---|---|---|
| 1 | 0.38 | 2477 |
| 1 | 0.38 | 2277 |
| 1 | 0.38 | 2414 |
| 2 | 0.10 | 33 |
| 2 | 0.10 | 1764 |
| 2 | 0.10 | 2414 |
| 3 | 0.02 | 34 |
| 3 | 0.02 | 31 |
| 3 | 0.02 | 29 |
| Negative Control | | 77 |
| Negative Control | | 70 |
| Negative Control | | 89 |
| Positive Control | | 1876 |
| Positive Control | | 1987 |
| Positive Control | | 1919 |

B. Sensitivity of the C. pneumoniae 76kD Primers and Probe

The 76kD primers (SEQ ID NO 9 and SEQ ID NO 10) and 76kD detection probe (SEQ ID NO 11), described in Example 1, were used to amplify and detect a quantified panel of C. pneumoniae cells (TABLE 5) by the unit dose method described in Example 4.A. above. The primers were used at a concentration of 0.3 µM and the detection probe was used at a concetration of 8 nM. The other reaction mixture components were the same as in 4.A. above with the exception of $MgCl_2$ which was used at a final concentration of 1 mM.

The reaction mixture was amplified, followed by probe oligo hybridization as in 4.A. above.

Following probe hybridization, reaction products were detected on the Abbott LCx® system. The data from this experiment is presented in TABLE 5 and shows detection of C. pneumoniae at concentrations as low as 0.05 IFU/reaction.

TABLE 5

| Sample # | C. pneumoniae (IFU/reaction) | LCx ® rate (c/s/s) |
|---|---|---|
| 1 | 50000.00 | 1657 |
| 2 | 12500.00 | 1776 |
| 3 | 15625.00 | 1686 |
| 4 | 3906.25 | 1624 |
| 5 | 976.56 | 1685 |
| 6 | 244.14 | 1646 |
| 7 | 61.04 | 4688 |
| 8 | 15.26 | 1622 |
| 9 | 3.81 | 1628 |
| 10 | 0.95 | 1522 |
| 11 | 0.06 | 21 |
| 12 | 0.05 | 984 |
| Negative Control | | 41 |
| Positive Control | | 576 |

Additional testing was performed in triplicate at concentrations below 1 IFU/reaction. The results shown in TABLE 6 indicate consistent detection of C. pneumoniae at concentrations of 0.38 IFU/reaction.

TABLE 6

| Sample # | C. pneumoniae (IFU) | LCx ® rate (c/s/s) |
| --- | --- | --- |
| 1 | 0.38 | 1488 |
| 1 | 0.38 | 1410 |
| 1 | 0.38 | 1378 |
| 2 | 0.10 | 26 |
| 2 | 0.10 | 25 |
| 2 | 0.10 | 560 |
| 3 | 0.02 | 27 |
| 3 | 0.02 | 21 |
| 3 | 0.02 | 31 |
| Negative Control | | 26 |
| Negative Control | | 30 |
| Negative Control | | 34 |
| Positive Control | | 1531 |
| Positive Control | | 1572 |
| Positive Control | | 47 |

Example 5

Sensitivity and Specificity of C. pneumoniae OMP and 76kD Primers and Probes

The OMP primers (SEQ ID NO 2 and SEQ ID NO 3) and OMP detection probe (SEQ ID NO 4) or the 76kD primers (SEQ ID NO 9 and SEQ ID NO 10) and 76KD detection probe (SEQ ID NO 11), as described in Example 1, were used to amplify and detect previously quantified genomic DNA from both C. pneumoniae and Mycoplasma pneumoniae (M. pneumoniae), using the respective methods in Example 4 above. The data from this experiment is presented in TABLE 7 and shows detection of C. pneumoniae by both OMP and 76kD primer/probe sets at genomic DNA of 15.6 pg/ml, with no cross-detection of M. pneumoniae genomic DNA.

TABLE 7

| Sample | Genomic DNA (pg/ml) | OMP LCx ® rate (c/s/s) | 76kD LCx ® rate (c/s/s) |
| --- | --- | --- | --- |
| C. pneumoniae | 5000 | 2417 | 1864 |
| | 1250 | 2438 | 1882 |
| | 312 | 2543 | 1827 |
| | 78 | 2420 | 1772 |
| | 15.6 | 2481 | 1653 |
| M. pneumoniae | 5000 | 37 | 20 |
| | 1250 | 38 | 22 |
| | 312 | 46 | 18 |
| | 78 | 34 | 26 |
| | 15.6 | 41 | 30 |
| Buffer | 0 | 38 | 21 |

Example 6

Comparison of C. pneumoniae Detection by OH-PCR and Culture

A. OH-PCR and Culture Detection of C. pneumoniae in nasopharyngeal swab samples.

Test results from twenty-five nasopharyngeal swab samples obtained from patients that were tested for C. pneumoniae by traditional culture methodology were compared to results obtained using OMP primers (SEQ ID NO 2 and SEQ ID NO 3) and OMP detection probe (SEQ ID NO 4) or the 76kD primers (SEQ ID NO 9 and SEQ ID NO 10) and 76kD detection probe (SEQ ID NO 11) as described in Example 1. Sample DNA was isolated using the QIAgen nucleic acid purification method and amplified and detected by the respective OMP or 76kD methods as in Example 4 above. Results are shown in Table 8. C. pneumoniae was used as a positive control and salmon sperm DNA was used as a negative control.

TABLE 8

| Sample # | Culture | OMP LCx ® rate (c/s/s) | 76kD LCx ® rate (c/s/s) |
| --- | --- | --- | --- |
| 1 | – | 23 | 32 |
| 2 | – | 952 | 644 |
| 3 | – | 18 | 24 |
| 4 | – | 37 | 24 |
| 5 | – | 20 | 26 |
| 6 | – | 1499 | 2180 |
| 7 | – | 23 | 25 |
| 8 | – | 24 | 19 |
| 9 | – | 23 | 24 |
| 10 | – | 23 | 25 |
| 11 | – | 29 | 22 |
| 12 | + | 1538 | 2188 |
| 13 | – | 14 | 24 |
| 14 | – | 25 | 25 |
| 15 | + | 1510 | 2264 |
| 16 | + | 1670 | 2190 |
| 17 | + | 1532 | 2140 |
| 18 | + | 1455 | 2107 |
| 19 | – | 22 | 28 |
| 20 | + | 1609 | 2258 |
| 21 | + | 1580 | 2237 |
| 22 | + | 1525 | 2226 |
| 23 | – | 19 | 20 |
| 24 | + | 2348 | 1393 |
| 25 | + | 2215 | 1464 |
| Neg Control | | 24 | 85 |
| Neg Control | | 78 | 30 |
| Pos Control | | 1568 | 2061 |
| Pos Control | | 2048 | 1353 |

Ten samples were identified as positive for C. pneumoniae by culture (#12, 15, 16, 17,18, 20, 21, 22, 24 and 25), all of which were also detected as positive by both OMP and 76kD assay methods. Two additional samples (#2 and 6) were found positive by both the OMP and 76kD C. pneumoniae primer/probe sets using OH-PCR on the LCx®.

B. Detection of C. pneumoniae in Throat Swab and Nasopharyngeal Swab Samples Using the OMP Primer/Probe Set and Culture Eighteen paired throat swab and nasopharyngeal swab samples obtained from patients were tested for C. pneumoniae by traditional culture methodology and compared to C. pneumoniae detection using OMP primers (SEQ ID NO 2 and SEQ ID NO 3) and OMP detection probe (SEQ ID NO 4) as described in Example 1. Sample DNA was isolated using the QIAgen nucleic acid purification method and amplified and detected by the OMP method as in Example 4.A. above.

The results using the OMP C. pneumoniae primer/probe set showed concordance with standard culture, with all samples negative by both methods.

While the invention has been described in detail and with reference to specific embodiments, it will be apparent to one skilled in the art that various changes and modifications may be made to such embodiments without departing from the spirit and scope of the invention.

What is claimed is:

1. A set of oligonucleotides selected from the group consisting of: SEQ ID NOs. 2 and 5; SEQ ID NOs. 3 and 4; SEQ ID NOs. 2, 3 and 4; SEQ ID NOs. 2, 3 and 5; SEQ ID NOs. 2, 3, 4 and 5; SEQ ID NOs. 9 and 10; SEQ ID NOs. 10 and 12; SEQ ID NOs. 9, 10 and 11; SEQ ID NOs. 9, 10 and 12; SEQ ID NOs. 9, 10, 11 and 12; wherein said set of oligonucleotides detects 5000 pg/ml of *C. pneumoniae* nucleic acid in a test sample.

2. A method of detecting the presence of *C. pneumoniae* in a test sample without detecting *C. trachomatis* or *C. psittaci,* said method comprising the steps of:

a) contacting said test sample with an oligonucleotide set of claim 1; and b) detecting hybridization between said oligonucleotide and a *C. pneumoniae* target sequence as an indication of the presence of *C. pneumoniae* in said test sample.

3. The method of claim 2 wherein said oligonucleotide is labeled.

4. A method for detecting the presence of *C. pneumoniae* in a test sample comprising the steps of:

a) forming a reaction mixture comprising nucleic acid amplification reagents, a test sample containing a *C. pneumoniae* target sequence, and at least one primer and one probe oligonucleotide selected from the group consisting of SEQ ID NOs. 2 and 5; SEQ ID NOs. 3 and 4; SEQ ID NOs. 2, 3 and 4; SEQ ID NOs. 2, 3 and 5; SEQ ID NOs. 2, 3, 4 and 5; SEQ ID NOs. 9 and 10; SEQ ID NOs. 10 and 12; SEQ ID NOs. 9, 10 and 11; SEQ ID NOs. 9, 10 and 12; SEQ ID NOs. 9, 10, 11 and 12; wherein the set of primers and probes detects 5000 pg/ml of *C. pneumoniae* nucleic acid in said test sample; and b) subjecting said mixture to hybridization and extension conditions to generate at least one nucleic acid sequence complementary to said target sequence;

c) hybridizing said probe to said nucleic acid complementary to said target sequence, so as to form a hybrid comprising said probe and said nucleic acid; and d) detecting said hybrid as an indication of the presence of *C. pneumoniae* in said sample.

5. The method of claim 4 wherein said probe is labeled.

6. The method of claim 4 wherein said probe is labeled with a capture label and said primer is labeled with a detection label.

7. The method of claim 4 wherein said probe is labeled with a detection label and said primer is labeled with a capture label.

8. A kit comprising:

a) the set of oligonucleotides of claim 2, and b) amplification reagents.

\* \* \* \* \*

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
       (A) LENGTH: 230 base pairs
       (B) TYPE: nucleic acid
       (C) STRANDEDNESS: double
       (D) TOPOLOGY: linear (ii) MOLECULE TYPE: genomic DNA (C. pneumoniae)

(xi) SEQUENCE DESCRIPTION: SEQ ID NO:1:

```
TAGAAATTTG CCAGTCCGTT CCAGAATACG CTACTGTAGG ATCTCCTTAC              50

CCTATTGAAA TCCTTGCTAT AGGCAAAAAA GATTGTGTTG ATGTTGTGAT             100

TACACAACAC CTACCTTGCG AAGCTGAATT CGTAAGCAGT GATCCAGAAA             150

CAACTCCTAC AAGTGATGGG AAATTAGTCT GGAAAATCGA TCGCCTGGGT             200

GCAGGAGATA AATGCAAAAT TACTGTATGG                                   230
```

(2) INFORMATION FOR SEQ ID NO:2:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: synthetic DNA (xi) SEQUENCE DESCRIPTION: SEQ ID NO:2:

```
CAGTCCGTTC CAGAATACGC TACTG                                         25
```

(2) INFORMATION FOR SEQ ID NO:3:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: synthetic DNA (xi) SEQUENCE DESCRIPTION: SEQ ID NO:3:

```
TGCATTTATC TCCTGCACCC AGG                                           23
```

(2) INFORMATION FOR SEQ ID NO: 4:

(i) SEQUENCE CHARACTERISTICS:
       (A) LENGTH: 20
       (B) TYPE:  nucleic acid
       (C) STRANDEDNESS:  single
       (D) TOPOLOGY:  linear (ii) MOLECULE TYPE: synthetic DNA (xi) SEQUENCE DESCRIPTION: SEQ ID NO: 4:

```
CCAGAAACAA CTCCTACAAG                                               20
```

(2) INFORMATION FOR SEQ ID NO:5:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:5:

CTTGTAGGAG TTGTTTCTGG                                              20

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:6:

CAGTAGCGTA TTCTGGAACG GACTG                                        25

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: SINGLE
        (D) TOPOLOGY: linear (ii) MOLECULE TYPE: synthetic DNA (xi) SEQUENCE DESCRIPTION: SEQ ID NO:7:

CCTGGGTGCA GGAGATAAAT GCA                                          23

(2) INFORMATION FOR SEQ ID NO:8:

(i) SEQUENCE CHARACTERISTICS:
        (A) LENGTH: 150 base pairs
        (B) TYPE: nucleic acid
        (C) STRANDEDNESS: double
        (D) TOPOLOGY: linear (ii) MOLECULE TYPE: genomic DNA (C. pneumoniae)

(xi) SEQUENCE DESCRIPTION: SEQ ID NO:8:

TACCTCAACA TCACTAGCTG ACATACAGGC TGCTTTGGTG AGCCTCCAGG              50

ATGCTGTCAC TAATATAAAG GATACAGCGG CTACTGATGA GGAAACCGCA             100

ATCGCTGCGG TGTGGGAAAC TAAGAATGCC GATGCAGTTA AAGTTGGCGC             150

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:9:

CTAGCTGACA TACAGGCTGC TTTGG                                        25

(2) INFORMATION FOR SEQ ID NO:10:

(i) SEQUENCE CHARACTERISTICS:

(A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:10:

CATCGGCATT CTTAGTTTCC CACTC                                              25

(2) INFORMATION FOR SEQ ID NO:11:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:11:

TTCCTCATCA GTAGCC                                                        16

(2) INFORMATION FOR SEQ ID NO:12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:12:

GGCTACTGAT GAGGAA                                                        16

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:13:

CCAAAGCAGC CTGTATGTCA GCTAG                                              25

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:14:

GAGTGGGAAA CTAAGAATGC CGATG                                              25